(12) United States Patent
Strzepa et al.

(10) Patent No.: US 8,012,217 B2
(45) Date of Patent: Sep. 6, 2011

(54) TALAR IMPLANTS AND METHODS OF USE

(75) Inventors: Peter Strzepa, Austin, TX (US);
Stephen D Cook, New Orleans, LA (US)

(73) Assignee: Fellowship of Orthopaedic Researchers, LLC, Metairie, LA (US)

( * ) Notice: Subject to any disclaimer, the term of this patent is extended or adjusted under 35 U.S.C. 154(b) by 233 days.

(21) Appl. No.: 12/319,869

(22) Filed: Jan. 13, 2009

(65) Prior Publication Data
US 2010/0004743 A1 Jan. 7, 2010

Related U.S. Application Data

(60) Provisional application No. 61/078,095, filed on Jul. 3, 2008.

(51) Int. Cl.
*A61F 2/42* (2006.01)
(52) U.S. Cl. .................................................. 623/21.18
(58) Field of Classification Search ............... 623/14.12, 623/19.13, 21.18
See application file for complete search history.

(56) References Cited

U.S. PATENT DOCUMENTS

| | | | |
|---|---|---|---|
| 4,021,864 A * | 5/1977 | Waugh | ......... 623/21.18 |
| 4,158,894 A | 6/1979 | Worrell | |
| 4,231,121 A | 11/1980 | Lewis | |
| 4,281,419 A | 8/1981 | Treace | |
| 4,849,692 A | 7/1989 | Blood | |
| 4,919,667 A | 4/1990 | Richmond | |
| 4,945,305 A | 7/1990 | Blood | |
| 4,964,867 A | 10/1990 | Boger | |
| 5,019,104 A | 5/1991 | Whiteside et al. | |
| 5,236,462 A | 8/1993 | Mikhail | |
| 5,246,460 A | 9/1993 | Goodfellow et al. | |
| 5,306,311 A | 4/1994 | Stone | |
| 5,358,525 A | 10/1994 | Fox | |
| 5,580,353 A | 12/1996 | Mendes et al. | |
| 5,600,330 A | 2/1997 | Blood | |
| 5,609,640 A | 3/1997 | Johnson | |

(Continued)

FOREIGN PATENT DOCUMENTS

CA 2232068 3/1997

(Continued)

OTHER PUBLICATIONS

On-X Carbon Properties, http://www.onxlti.com/onxlti-cm-carbon-prop.html, Nov. 15, 2010.*

(Continued)

*Primary Examiner* — Corrine M McDermott
*Assistant Examiner* — Megan Wolf
(74) *Attorney, Agent, or Firm* — Greenberg Traurig, LLP

(57) ABSTRACT

Implant devices, and method of using the same, are provided. The implant devices have a head and a stem. The head has an upper surface, an anterior surface, a posterior surface, a lateral surface and a lower surface. The anterior surface, the lateral surface, and the lower surface are approximately perpendicular to and intersect each other. The anterior surface and the posterior surface are approximately parallel to each other. Preferably, the upper surface has a general shape of at least a portion of a superior articular surface of a talus and at least a portion of a medial articular surfaces of a talus. The stem has a truncated conical portion and a cylindrical portion. The cylindrical portion is affixed to the lower surface of the head, and the truncated conical portion is affixed to the cylindrical portion.

18 Claims, 3 Drawing Sheets

U.S. PATENT DOCUMENTS

| | | | |
|---|---|---|---|
| 5,645,605 A | | 7/1997 | Klawitter |
| 5,742,394 A | | 4/1998 | Hansen |
| 5,744,953 A | | 4/1998 | Hansen |
| 5,749,874 A | | 5/1998 | Schwartz |
| 5,766,259 A | * | 6/1998 | Sammarco ................ 623/21.18 |
| 5,767,669 A | | 6/1998 | Hansen et al. |
| 5,767,960 A | | 6/1998 | Orman et al. |
| 5,782,835 A | | 7/1998 | Hart |
| 5,782,927 A | | 7/1998 | Klawitter et al. |
| 5,824,095 A | * | 10/1998 | Di Maio et al. ............ 623/18.11 |
| 5,831,260 A | | 11/1998 | Hansen |
| 5,953,683 A | | 9/1999 | Hansen et al. |
| 6,159,247 A | | 12/2000 | Klawitter et al. |
| 6,172,499 B1 | | 1/2001 | Ashe |
| 6,183,519 B1 | * | 2/2001 | Bonnin et al. ............ 623/21.18 |
| 6,217,616 B1 | | 4/2001 | Ogilvie |
| 6,246,231 B1 | | 6/2001 | Ashe |
| 6,417,839 B1 | | 7/2002 | Odell |
| 6,436,146 B1 | | 8/2002 | Hassler et al. |
| 6,473,167 B1 | | 10/2002 | Odell |
| 6,528,991 B2 | | 3/2003 | Ashe |
| 6,575,986 B2 | | 6/2003 | Overaker |
| 6,610,067 B2 | | 8/2003 | Tallarida et al. |
| 6,626,945 B2 | | 9/2003 | Simon |
| 6,626,950 B2 | | 9/2003 | Brown |
| 6,663,669 B1 | * | 12/2003 | Reiley ........................ 623/21.18 |
| 6,679,917 B2 | | 1/2004 | Ek |
| 6,699,292 B2 | | 3/2004 | Ogilvie et al. |
| 6,709,460 B2 | | 3/2004 | Merchant |
| D490,900 S | | 6/2004 | Ogilvie et al. |
| 6,754,596 B2 | | 6/2004 | Ashe |
| 6,784,660 B2 | | 8/2004 | Ashe |
| 6,797,006 B2 | | 9/2004 | Hodorek |
| 6,814,757 B2 | | 11/2004 | Kopylov et al. |
| 6,815,651 B2 | | 11/2004 | Odell |
| 6,856,823 B2 | | 2/2005 | Ashe |
| 7,027,634 B2 | | 4/2006 | Odell |
| 7,106,431 B2 | | 9/2006 | Odell |
| 7,161,686 B2 | | 1/2007 | Duling et al. |
| 7,204,854 B2 | | 4/2007 | Guederian et al. |
| 7,264,634 B2 | | 9/2007 | Schmieding |
| 7,314,488 B2 | | 1/2008 | Reiley |
| 2003/0135280 A1 | | 7/2003 | Kopylov et al. |
| 2003/0233149 A1 | | 12/2003 | Hodorek |
| 2004/0039447 A1 | | 2/2004 | Simon et al. |
| 2004/0230303 A1 | | 11/2004 | Gomes et al. |
| 2004/0230315 A1 | | 11/2004 | Ek |
| 2005/0033426 A1 | | 2/2005 | Ogilvie et al. |
| 2005/0084513 A1 | | 4/2005 | Tang |
| 2005/0137708 A1 | | 6/2005 | Clark |
| 2005/0137713 A1 | | 6/2005 | Bertram |
| 2006/0069446 A1 | | 3/2006 | Ragusa et al. |
| 2006/0190002 A1 | | 8/2006 | Tallarida et al. |
| 2006/0229726 A1 | | 10/2006 | Ek |
| 2006/0241778 A1 | | 10/2006 | Ogilvie |
| 2007/0005143 A1 | | 1/2007 | Ek et al. |
| 2007/0032876 A1 | | 2/2007 | Clark |
| 2007/0078334 A1 | | 4/2007 | Scully et al. |
| 2007/0123993 A1 | | 5/2007 | Hassler et al. |
| 2007/0198095 A1 | | 8/2007 | VanDer Meulen et al. |
| 2007/0225820 A1 | | 9/2007 | Thomas et al. |
| 2007/0250169 A1 | | 10/2007 | Lang |
| 2008/0188942 A1 | | 8/2008 | Brown et al. |
| 2009/0240336 A1 | * | 9/2009 | Vander Meulen et al. . 623/18.11 |

FOREIGN PATENT DOCUMENTS

| | | |
|---|---|---|
| DE | 69732500 T | 4/2006 |
| DE | 69732500 T2 | 4/2006 |
| DE | 602004003510 | 8/2007 |
| DE | 602004003510 T | 8/2007 |
| DE | 60126129 T | 11/2007 |
| DE | 60126129 T2 | 11/2007 |
| EP | 1112753 A1 | 2/2001 |
| EP | 1437104 | 7/2004 |
| EP | 1437104 A1 | 7/2004 |
| EP | 1955676 A1 | 8/2008 |
| ES | 2141533 | 3/2000 |
| ES | 2141533 T | 3/2000 |
| JP | 2004202233 A | 7/2004 |
| WO | WO-8802844 | 4/1988 |
| WO | WO-9012276 | 10/1990 |
| WO | WO-9203117 | 3/1992 |
| WO | WO-9602008 | 1/1996 |
| WO | WO-9710780 | 3/1997 |
| WO | WO-9819637 | 5/1998 |
| WO | WO-0013617 | 3/2000 |
| WO | WO-0133162 | 5/2001 |
| WO | WO-0133162 A1 | 5/2001 |
| WO | WO-0170138 | 9/2001 |
| WO | WO-0170138 A1 | 9/2001 |
| WO | WO-0243627 | 6/2002 |
| WO | WO-0243627 A1 | 6/2002 |
| WO | WO-2004093767 | 11/2004 |
| WO | WO-2004093767 A1 | 11/2004 |
| WO | WO-2007041678 | 4/2007 |
| WO | WO-2007041678 A2 | 4/2007 |
| WO | WO-2007059459 | 5/2007 |
| WO | WO-2007059459 A2 | 5/2007 |
| WO | WO-2007103362 | 9/2007 |
| WO | WO-2007103362 A2 | 9/2007 |
| WO | WO-2007109752 | 9/2007 |
| WO | WO-2007109752 A2 | 9/2007 |

OTHER PUBLICATIONS

PCT International Search Report of the International Searching Authority for International Application No. PCT/US2009/049441.

PCT Written Opinion of the International Searching Authority for International Application No. PCT/US2009/049441.

"Pyrocarbon in Orthopedics", downloaded from www.pyrocarbon. com/pyrocarbon-orthopedic-implants.php on Feb. 12, 2008, pp. 1-4.

"Pyrolytic Carbon" downloaded from http://en.wikipedia.org/wiki/Pyrolytic_carbon on Feb. 12, 2008, p. 1-2.

PCT International Search Report for International Application No. PCT/US09/36159.

PCT Written Opinion of the International Searching Authority for International Application No. PCT/US09/36159.

"Pyrocarbon in Orthopedics", downloaded from www.pyrocarbon. com/pyrocarbon-orthopedic-implants.php on Feb. 12, 2008, pp. 1-4.

"Pyrolytic Carbon" downloaded from http://en.wikipedia.org/wiki/Pyrolytic_carbon on Feb. 12, 2008, p. 1-2.

PCT International Search Report Issued in Connection with International Application No. PCT/US2010/046654; Nov. 29, 2010; 1-5 pages.

PCT Written Opinion of the International Searching Authority Issued in Connection with International Application No. PCT/US2010/046654; Nov. 29, 2010; 1-8 pages.

Non-Final Office Action Issued Against U.S. Appl. No. 12/074,770; Nov. 24, 2010; 1-14 pages.

* cited by examiner

TALAR IMPLANTS AND METHODS OF USE

CROSS-REFERENCE TO RELATED APPLICATIONS

This patent application claims the benefit of U.S. Provisional Patent Application No. 61/078,095 filed Jul. 3, 2008.

FIELD OF THE INVENTION

This invention relates to devices and methods for the repair of articular cartilage defects. In particular embodiments of, this invention relates to new and improved implants that serve as a replacement for diseased or damaged cartilage in joints such as human ankles, and in more particularity talar cartilage.

BACKGROUND OF THE INVENTION

Cartilage acts as a pad between bones to reduce friction and prevent the bones from grinding against one another. Cartilage covers the articular surface of many, if not all, joints in the body. The smoothness and thickness of the cartilage are factors that determine the load-bearing characteristics and mobility of the joints. Over time, due to injury or heredity, however, lesions such as fissures, cracks or crazes can form in the cartilage. In some cases, osteochondral, the lesion penetrates to the subchondral surface of the bone. In other cases, chondral, the lesion does not penetrate to the subchondral surface of the bone. In any event, lesions generally do not repair. themselves—and if any repair is made it is generally insufficient to heal—leading to significant pain and disability, either acutely or over time. Thus, there has long been a need to treat, repair, or regenerate damaged articular cartilage.

One approach for regenerating new cartilage is autologous chondrocyte transplantation. However, this technique is complex and relatively costly. Other techniques, aimed at repair instead of regeneration, include debridement, lavage, microfracturing, drilling, and abrasion arthroplasty. These procedures generally involve penetrating the region of vascularization in the subchondral bone with an instrument until bleeding occurs. Formation of a fibrin clot differentiates into fibrocartilage, which then covers the defect site. Some have found, however, that the resulting repair tissue is relatively weak, disorganized, and lacks the biomechanical properties of normal hyaline cartilage that typically covers the bone ends. Additionally, this technique can generally only be used on chondral defects in the presence of normal joint congruity.

An alternative approach has been to undergo a total replacement of the joint. Such total replacements, however, are costly, high risk, and involve a long recovery time.

SUMMARY OF THE INVENTION

Definitions

In various illustrating embodiments, the term "torus" means the surface of a toriod.

In various illustrating embodiments, the term "tubular radius" refers to the radius of the tube of a torus, as opposed to the "major radius," which refers to the radius from the center of the torus to the center of the tube.

In various illustrating embodiments, geometric terms such as "circle", "circular," "cylinder", "cylindrical," "cone," "conical," "normal," and the like are used as references and for clarity of understanding, as would be understood by one of ordinary skill in the art. Accordingly, these terms should not be limited to strict Euclidean standards.

Various illustrating embodiments of the present invention provide implant devices, preferably for use in human joints, including the talus. In accordance with one aspect of an illustrating embodiment of the present invention a implant is provided which includes a head and a stem. The head is bounded by an upper surface, an anterior surface, a posterior surface, a lateral surface and a lower surface. The anterior surface, the lateral surface, and the lower surface are each flat, approximately perpendicular to each other and intersect each other, thus forming edges of the head. The anterior surface and the posterior surface are approximately parallel to each other and separated a distance from each other; the posterior surface intersects the upper surface and lateral surface and lower surface, thus forming additional edges of the head. Preferably, the upper surface has the general shape of portions of the superior and medial articular surfaces of a talus, which consist of the trochlea for the tibia, and the surface for the medial malleolus of the tibia. The stem has a cylindrical portion and a truncated conical portion. The cylindrical portion is affixed to and extends downward from the lower surface of the head, and the truncated conical portion is affixed to and extends downward from a lower end of the cylindrical portion.

In accordance with another aspect of an illustrating embodiment of the present invention, a method of repairing articular cartilage using the implant device is provided. The method of this illustrative embodiment includes locating articular cartilage having a lesion. An implant device, as described above, is selected preferably having dimensions compatible with the lesion. A hole is formed through the cartilage and subchondral bone, into the cancellous bone. The implant device may be inserted into the hole so that the lower, anterior, posterior and lateral surfaces of the head of the implant device abut against the prepared subchondral and cancellous bone and the stem of the implant device abuts against the prepared cancellous bone.

In the detailed description which follows in conjunction with the drawings, like parts are given like reference numerals, and the vertical, horizontal and depth orientations of a given embodiment are specified explicitly in at least one drawing of an illustrative embodiment.

BRIEF DESCRIPTION OF THE DRAWINGS

The drawing figures are not necessarily to scale and certain features of the invention may be shown exaggerated in scale or in somewhat schematic form in the interest of clarity and conciseness, wherein.

DISCLOSURE OF ALTERNATIVE EMBODIMENTS

Figure 1:
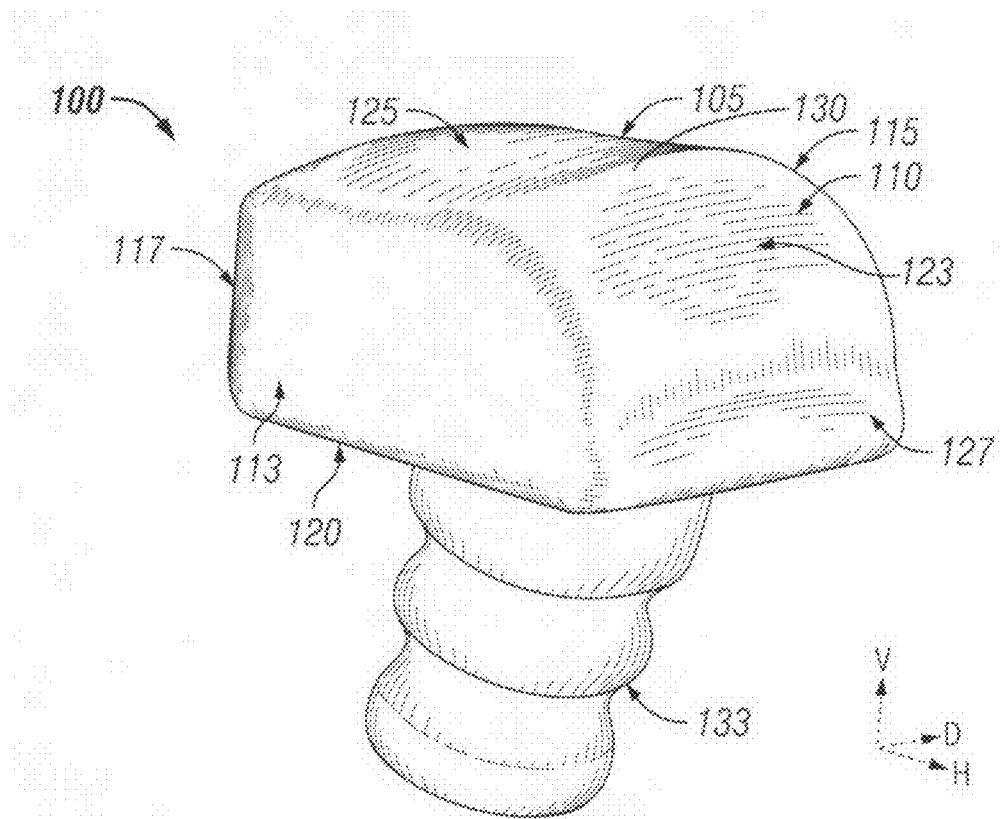
FIG. 1 is an angled view of one embodiment of an implant.

FIG. 1 is an illustrative embodiment of an implant 100, in which the vertical, V, horizontal, H, and depth, D, orientations of this embodiment are depicted. The implant 100 is preferably used to replace portions of the superior and medial articulating surfaces of the talus. The implant 100 includes a head 105 and a stem 133. The head 105 is preferably bound by five surfaces: an upper surface 110, an anterior surface 113, a posterior surface 115, a lateral surface 117, and a lower surface 120. The anterior surface 113, lateral surface 117, and lower surface 120 may be each flat and approximately perpendicular to one another. The anterior surface 113 and posterior surface 115 may be approximately parallel. All of the surfaces of the head 105 preferably blend into one another. The blend may have an edge radius of from about 0.1 millimeters to about 1 millimeter.

The upper surface 110 is preferably shaped to mimic portions of the superior and medial articular surfaces of a talus. For ease of reference, the upper surface 110 may be thought of as segmented into a first portion 123, a second portion 125, and a third portion 127. The first portion 123 may be tangent on its lateral edge to the second portion 125. The first portion 123 may also be tangent on its medial edge to the third portion 127. In an embodiment, with reference to FIG. 2, the first portion 123 is generally bounded on its lateral and medial edges by dashed lines A and B.

Figure 2:
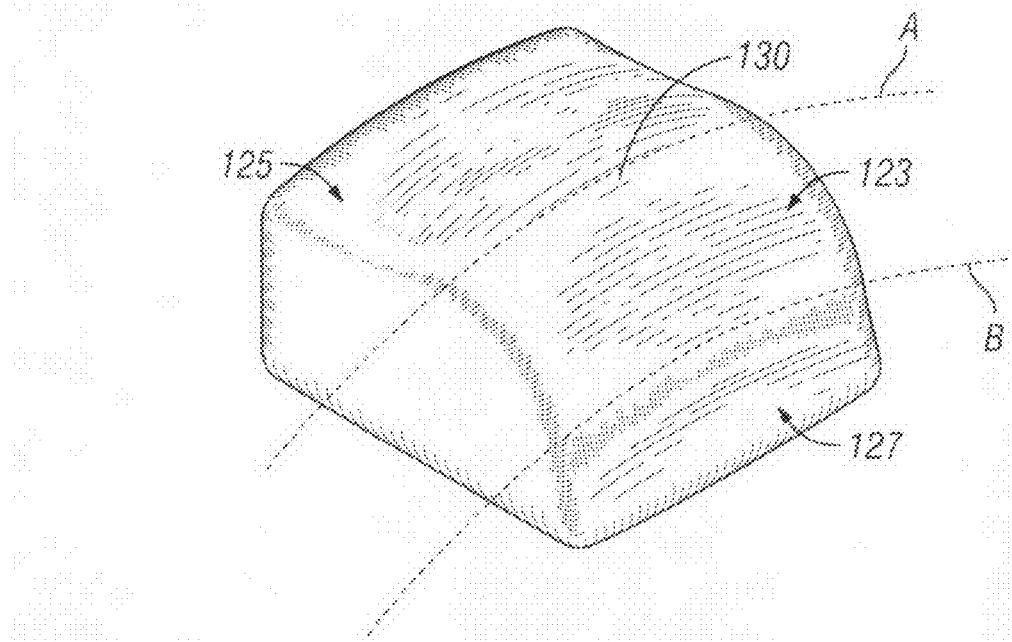
FIG. 2 is a segmented and exploded view of the head of the implant of FIG. 1.

With reference to FIGS. 1 and 2, the first portion 123 may be a convex surface having a generally toroidal shape with a major radius ranging from about 9 millimeters to about 31 millimeters, alternatively from about 14 millimeters to about 26 millimeters, and alternatively about 16 millimeters. The minor (tubular) radius of the first portion 123 may range from about 2 millimeters to about 6 millimeters, alternatively from about 3 millimeters to about 5 millimeters, and alternatively about 4 millimeters. The first portion 123 may have an apex point 130 which is the most superior point on the upper surface 110, and in an embodiment the apex point 130 is located equidistant from planes containing the anterior 113 and posterior 115 surfaces. The second portion 125 may be a generally convex-concave shape having a toroidal saddle shape. The toroidal saddle shape of the second portion 125 may have a major radius in its plane of convex curvature ranging from about 20 millimeters to about 100 millimeters, alternatively from about 40 millimeters to about 80 millimeters, and alternatively about 60 millimeters. The toroidal saddle shape of the second portion 125 may have a minor (tubular) radius in its plane of concave curvature ranging from about 10 millimeters to about 70 millimeters, alternatively from about 25 millimeters to about 55 millimeters, and alternatively about 40 millimeters. The third portion 127 may have the general shape of a portion of the surface of a right circular cone with a vertex angle ranging from about 60 degrees to about 89 degrees, alternatively from about 70 degrees to about 80 degrees, and alternatively about 75 degrees.

The distance normal to a plane containing the lateral surface 117 and terminating at the apex point 130 may range from about 2 millimeters to about 12 millimeters, alternatively from about 4 millimeters to about 10 millimeters, and alternatively from about 6 millimeters to about 8 millimeters. The distance normal to the lower surface 120 and terminating at the apex point 130 may range from about 2 millimeters to about 12 millimeters, alternatively from about 4 millimeters to about 10 millimeters, and alternatively from about 6 millimeters to about 8 millimeters. The distance normal from the anterior surface 113 to the posterior surface 115 may range from about 6 millimeters to about 18 millimeters, alternatively from about 8 millimeters to about 16 millimeters, and alternatively from about 10 millimeters to about 14 millimeters.

Figure 3:
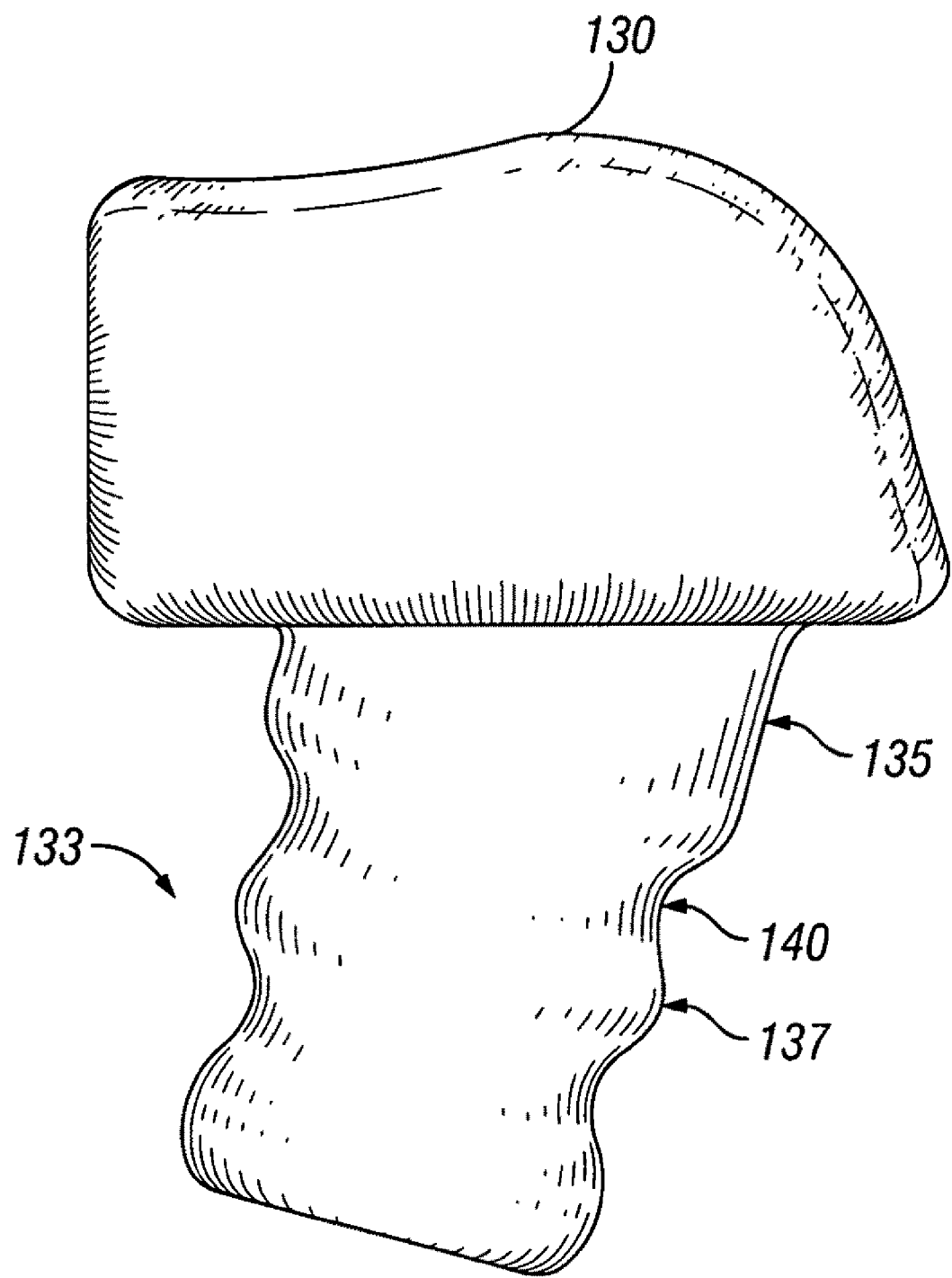
FIG. 3 is an end view of the implant of FIG. 1.
Figure 4:
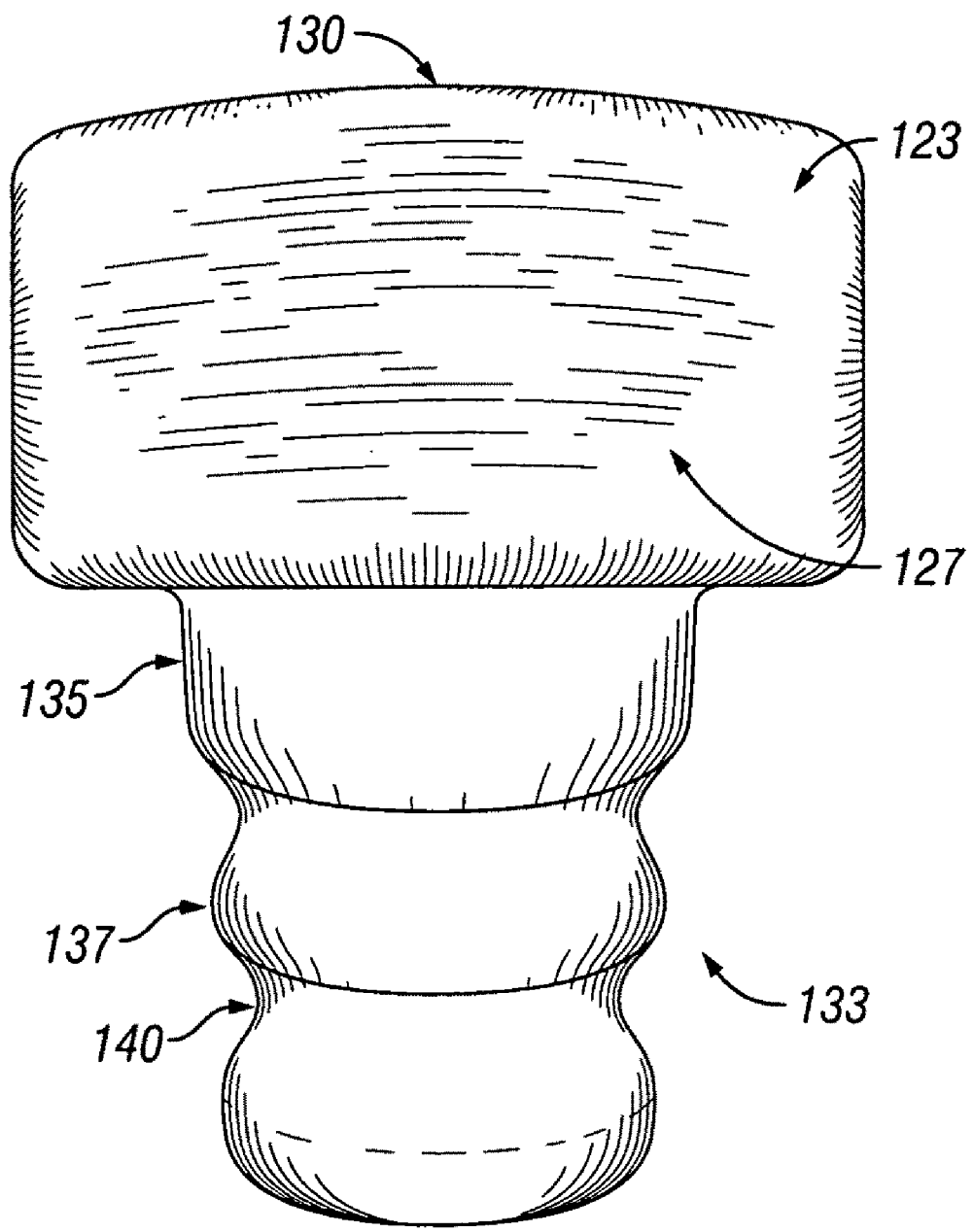
FIG. 4 is a side view of the implant of FIG. 1.

With reference to FIGS. 1, 3, and 4, the stem 133 may extend from the lower surface 120 of the head 105 in a general direction away from the third portion 127 of the upper surface 110. Preferably, the head 105 and stem 133 are formed as a non-modular, uni-body, i.e., one integral piece without no intervening mechanical connection. The stem may extend from the lower surface 120 of the head 105 in a general direction toward a plane containing the lateral surface 117 of the head 105. In this manner, the stem 133 may extend at an angle—relative to the normal to the lower surface 120 of the head 105—ranging from about 0 to about 45 degrees, alternatively from about 0 to about 30 degrees, and alternatively about 15 degrees.

The stem 133 may be of a single cylindrical or a single, truncated conical shape. Alternatively, the stem 133 may include two portions: an cylindrical portion 135 and a truncated conical portion 137. The cylindrical portion 135 may be adjacent to the lower surface 120 of the head 105, and of an approximate cylindrical shape, which extends in a direction away from the lower surface 120 of the head 105. The cylindrical portion 135 may have a diameter ranging from about 2 millimeters to about 12 millimeters, alternatively from about 4 millimeters to about 8 millimeters, and alternatively about 6 millimeters. The central length of the cylindrical portion 135 may range from about 0.1 millimeters to about 10 millimeters, alternatively from about 0.25 millimeters to about 5 millimeters, and alternatively from about 0.5 millimeters to about 3 millimeters. As the cylindrical portion 135 is preferably disposed at an angle, its central length will be greater than the minimum length along its outer surface and less than the maximum length along its outer surface. The lower surface 120 of the head 105 may blend into the cylindrical portion 135 of the stem 133 with a corner fillet. The corner fillet may have a radius of about 1.5 millimeters.

The truncated conical portion 137 may be adjacent to the cylindrical portion 135, and of an approximate truncated conical shape, which extends in a direction away from the cylindrical portion 135. The maximum diameter of the truncated conical portion 137 may be at its intersection with the cylindrical portion 135, and the maximum diameter of the truncated conical portion 137 may be equal to the diameter of the cylindrical portion 135. The diameter of the truncated conical portion 137 may decrease along a direction away from the cylindrical portion 135. The total included angle of the truncated conical portion 137 may range from about 0 degrees to about 15 degrees, alternatively from about 5 degrees to about 10 degrees, and alternatively about 7.5 degrees. The central length of the truncated conical portion 137 may range from about 0.1 millimeters to about 15 millimeters, alternatively from about 2 millimeters to about 12 millimeters, and alternatively from about 4 millimeters to about 10 millimeters.

The truncated conical portion 137 may include circumferential grooves 140 about its perimeter. The shape of the circumferential grooves 140 may be defined by a partial torus having a tubular radius ranging from about 0.25 millimeters to about 2 millimeters, alternatively from about 0.5 millimeters to about 1 millimeter, alternatively about 1 millimeter. The circumferential grooves 140 may be spaced apart at a distance ranging from about 1 millimeter to about 3 millimeters from each other, alternatively from about 2 millimeters to about 2.5 millimeters from each other along the central axis of the truncated conical portion. The circumferential grooves 140 may blend into the truncated conical portion 137 of the stem 133 with a blend having an edge radius of from about 0.1 millimeters to about 1 millimeters, alternatively about 0.8 millimeters.

The implant 100 many be manufactured from a variety of suitable materials, having the requisite strength and biocompatibility characteristics to function as an implant, including but not limited to any of the following, individually or in combination, graphite, pyrocarbon, ceramic, aluminum oxide, silicone nitride, silicone carbide or zirconium oxide; metal and metal alloys, e.g., Co—Cr—W—Ni, Co—Cr—Mo, CoCr alloys, CoCr molybdenum alloys, Cr—Ni—Mn alloys; powder metal alloys, 316L or other stainless steels, Ti and Ti alloys including Ti 6A1-4V ELI; polymers, e.g., polyurethane, polyethylene, polypropylene, thermoplastic elastomers, polyaryletherketones such as polyetherehterketone (PEEK) or polyetherketoneketone (PEKK); biomaterials such as polycaprolactone; and diffusion hardened materials such as Ti-13-13, zirconium and niobium. Moreover, the implant 100 may be coated with a variety of suitable materials, including any of the following, individually or in combination, porous coating systems on bone-contacting surfaces, hydrophilic coatings on load-bearing surfaces, hydroxyapatite coatings on bone-contacting surfaces, and tri-calcium phosphate on bone-contacting surfaces. Other suitable coatings include growth factors and other biological agents such as bone morphogenetic proteins (BMP's), transforming growth factor beta, among others. Additionally, components of the invention may be molded or cast, hand-fabricated or machined.

In an illustrative embodiment, the implant 100 is composed of graphite and pyrocarbon. Preferably, the implant 100 is graphite and includes a coating of pyrocarbon. The pyrocarbon coating may have an average thickness of from about 100 to about 1000 microns, alternatively from about 200 microns to about 500 microns, alternatively from about 250 to about 500 microns, alternatively about 350 microns. The pyrocarbon coating may have an elastic modulus from about 15 gigapascals ("GPa") to about 22 GPa, alternatively about 20 GPa. The pyrocarbon coating may further have a strength of at least 200 megapascals ("MPa"), alternatively at least about 300 MPa, alternatively at least about 400 MPa. The pyrocarbon elastic modulus and strength are preferably tested using four-point bend, third-point-loading substrated specimens of dimensions 25 millimeters by 6 millimeters by 0.4 millimeters. Preferably the pyrocarbon is pyrolytic carbon as described in *Pure Pyrolytic Carbon: Preparation and Properties of a New Material, On-X Carbon for Mechanical Heart Valve Prostheses*, Ely et al, J. Heart Valve Dis., Vol. 7, No. 6, A00534 (November 1998), alternatively pyrocarbon is pyrolytic carbon as described in the before-mentioned J. Heart Valve Dis. publication, but includes additional silicon.

The above-described implants may be used to repair damaged articular cartilage in humans, including ankles, knees, wrists, elbows, shoulders, and the like joints. In another illustrative embodiment or a preferred method, a patient having articular cartilage damage is identified. The patient is fully informed of the risks associated of surgery, and consents to the same. An incision is made near the damaged articular cartilage. The lesion to be repaired is identified, and a implant having dimensions compatible with the lesion is selected. The implant may be slightly smaller or slightly larger than the lesion. In these embodiments, the implant is from about 0.1 percent to about 20 percent smaller or larger than the lesion. A hole is then formed, i.e., drilled, punched, or broached, through the cartilage and the subchondral bone into the cancellous bone. Preferably, the dimensions of the hole are slightly less than the horizontal and depth dimensions of the stem of the implant. This may be achieved, for example, by using a box chisel and then a tapered dill bit. Preferably the minimum length of the hole is equal to or slightly greater than the length of the stem 133 of the implant 100, along the central axis of the stem. An amount of healthy and damaged cartilage may be removed near the lesion so that the lower surface 120 and lateral surface 117 of the head 105 may rest against the patient's bone. In this manner, however, it is preferable to remove as little healthy cartilage as possible. The stem 133 of the implant 100 may be inserted into the hole, and the lower surface 120 and lateral surface 117 of the implant's 100 head 105 may rest against the bone. The incision is then sutured by any of several known methods.

While specific alternatives to steps of the specific embodiments have been described herein, additional alternatives not specifically disclosed but known in the art are intended to fall within the scope of the invention. For example, while specific dimensions, and ranges of dimensions, have been provided further dimensions may reasonably fall within the scope of the invention. Thus, it is understood that other applications of the present invention will be apparent to those skilled in the art upon reading the descriptions of the described illustrative embodiments and after consideration of the appended claims and drawings.

The invention claimed is:

1. An implant comprising:
a head having an upper surface, an anterior surface, a posterior surface, a lateral surface, and a lower surface; the anterior surface, the lateral surface, and the lower surface are each flat, approximately perpendicular, and intersect each other;
the anterior surface and the posterior surface are approximately parallel to each other, wherein the upper surface has a general shape of at least a portion of a superior articular surface of a talus and at least a portion of a medial articular surfaces of a talus, wherein the upper surface includes a convex first portion having a generally toroidal shape, a second portion having a general toroidal saddle shape, and a third portion having a general shape of a portion of a surface of a right circular cone, wherein the first portion is tangent on its lateral edge to the second portion and the first portion is tangent on its medial edge to the third portion; and
a stem having a cylindrical portion and a truncated conical portion, the cylindrical portion affixed to and extending in a direction away from the lower surface of the head and the truncated conical portion affixed to and extending in a direction away from a lower end of the cylindrical portion.

2. The implant of claim 1, wherein the toroid of the convex first portion has a major radius ranging from about 9 millimeters to about 31 millimeters, and a minor tubular radius ranging from about 2 millimeters to about 6 millimeters.

3. The implant of claim 1, wherein the toroid of the second portion has a major radius in a plane of convex curvature ranging from about 20 millimeters to about 100 millimeters, and a minor tubular radius in a plane of concave curvature ranging from about 10 millimeters to about 70 millimeters.

4. The implant of claim 1, wherein the third portion has the general shape of a portion of a surface of a right circular cone having a vertex angle ranging from about 60 degrees to about 89 degrees.

5. The implant of claim 1, wherein an apex point is present on the upper surface convex first portion, a distance normal to a plane containing the lateral surface and terminating at the apex point ranges from about 2 millimeters to about 12 millimeters, a distance normal to the lower surface and terminating at the apex point ranges from about 2 millimeters to about 12 millimeters a distance normal from the anterior surface to the posterior surface ranges from about 6 millimeters to about 18 millimeters.

6. The implant of claim 1, wherein the stem extends away from the lower surface of the head in a direction away form the third portion of the upper surface and toward the lateral surface of the head at an angle ranging from about 0 to about 45 degrees, wherein the angle is referenced to the normal to the lower surface of the head.

7. The implant of claim 1, wherein the cylindrical portion has a diameter ranging from about 2 millimeters to about 12 millimeters, and a central length of the cylindrical portion ranges from about 0.1 millimeters to about 10 millimeters.

8. The implant of claim 1, wherein a total included angle of the truncated conical portion ranges from about 0 degrees to about 15 degrees, and a central length of the truncated conical portion ranges from about 0.1 millimeters to about 15 millimeters.

9. The implant of claim 8, wherein the truncated conical portion has a plurality of circumferential grooves about its perimeter, the circumferential grooves are defined by a partial torus having a tubular radius ranging from about 0.25 millimeters to about 2 millimeters, and the circumferential grooves are spaced apart at a distance ranging from about 1 millimeter to about 3 millimeters from each other along the central axis of the stem.

10. The implant of claim 9, wherein the circumferential grooves blend into the truncated conical portion of the stem and have an edge radius ranging from about 0.1 millimeters to about 1 millimeters.

11. The implant of claim 1, wherein the anterior surface blends into the upper surface, the lateral surface, and the lower surface; the posterior surface blends into the upper surface, the lateral surface, and the lower surface; the lower surface blends into the upper surface, the anterior surface, the posterior surface, and the lateral surface; the lateral surface blends into the upper surface, the lower surface, the anterior surface, and the posterior surface, and wherein each blend has an edge radius of from about 0.1 millimeters to about 1 millimeter.

12. The implant of claim 1, wherein the lower surface of the head blends into the cylindrical portion of the stem with a corner fillet, the corner fillet having a radius of about 1.5 millimeters.

13. The implant of claim 1, wherein the head and the stem are formed from graphite and pyrocarbon.

14. The implant of claim 13, wherein the head and the stem comprise a graphite core and a pyrocarbon coating, the pyrocarbon coating having an elastic modulus from about 15 GPa to about 22 GPa, the pyrocarbon coating having an average thickness ranging from about 100 to about 1000 microns.

15. The implant of claim 14, wherein the pyrocarbon coating has an elastic modulus of about 20 GPa and a strength of at least 400 MPa.

16. The implant of claim 15, wherein the upper surface has contiguous edge blends, which are polished, and the lower surface and stem are coated with hydroxyapatite.

17. A method of repairing articular cartilage comprising:
locating articular cartilage having a lesion;
utilizing an implant having dimensions compatible with the lesion, wherein the implant comprises:
a head having an upper surface, an anterior surface, a posterior surface, a lateral surface, and a lower surface;
the anterior surface, the lateral surface, and the lower surface are each flat, approximately perpendicular and intersect each other;
the anterior surface and the posterior surface are approximately parallel to each other, wherein the upper surface has a general shape of at least a portion of a superior articular surface of a talus and at least a portion of a medial articular surfaces of a talus, wherein the upper surface includes a convex first portion having a generally toroidal shape, a second portion having a general toroidal saddle shape, and a third portion having a general shape of a portion of a surface of a right circular cone, wherein the first portion is tangent on its lateral edge to the second portion and the first portion is tangent on its medial edge to the third portion; and
a stem having a cylindrical portion and a truncated conical portion, the cylindrical portion affixed to and extending in a direction away from the lower surface of the head and the truncated conical portion affixed to and extending in a direction away from a lower end of the cylindrical portion;
forming a cavity in the articular cartilage, subchondral bone, and cancellous bone; and
engaging the implant with the cavity so that the lower surface, anterior surface, posterior surface, and lateral surface abuts against the subchondral and cancellous bone and the stem abuts against the cancellous bone.

18. The method of claim 17, wherein forming the cavity includes placement of autograft, allograft bone, or various bone graft substitute material into the lesion.

* * * * *